United States Patent [19]

Kukolja et al.

[11] 3,962,226

[45] June 8, 1976

[54] 3-NITROOXYCEPHAM COMPOUNDS AND PROCESS FOR PREPARING DESACETOXYCEPHALOSPORINS THEREFROM

[75] Inventors: Stjepan P. Kukolja, Indianapolis; Steven R. Lammert, Greenwood, both of Ind.

[73] Assignee: Eli Lilly and Company, Indianapolis, Ind.

[22] Filed: Mar. 27, 1974

[21] Appl. No.: 455,443

Related U.S. Application Data

[63] Continuation-in-part of Ser. No. 267,850, June 30, 1972, abandoned.

[52] U.S. Cl. ............................. 260/243 C; 424/246; 424/271; 260/239.1
[51] Int. Cl.² ................ C07D 499/04; C07D 501/02
[58] Field of Search ..................... 260/239.1, 243 C

[56] References Cited

UNITED STATES PATENTS 3,852,282   12/1974   Dolfini ........................... 260/243 C

*Primary Examiner*—Nicholas S. Rizzo
*Attorney, Agent, or Firm*—William C. Martens, Jr.; Everet F. Smith

[57] ABSTRACT

A 3α-methyl-3β-halocepham compound and/or a 2α-methyl-2β-halomethylpenam compound is converted to a mixture comprising a 3-methyl-3-cephem (desacetoxycephalosporin), a 3α-methyl-3β-nitrooxycepham, and a 2α-methyl-2β-nitrooxymethylpenam by reaction of said halocepham compound and/or said halomethylpenam compound with silver nitrate. The novel 3-nitrooxycepham compound upon heating is converted to a desacetoxycephalosporin.

31 Claims, No Drawings

3-NITROOXYCEPHAM COMPOUNDS AND PROCESS FOR PREPARING DESACETOXYCEPHALOSPORINS THEREFROM

CROSS REFERENCE

This application is a continuation-in-part of application Ser. No. 267,850, filed June 30, 1972 and now abandoned.

BACKGROUND OF THE INVENTION

The cephalosporin antibiotics have recently achieved considerable success as therapeutic agents for the treatment of infectious diseases of man. This class of antibiotics is produced by two known general methods. In the first of these methods, cephalosporin C is produced by culturing the organism *Cephalosporium acremonium*, Newton and Abraham, Biochem. J., 62, 651 (1956). Cleavage of the α-aminoadipoyl side chain of cephalosporin C according to the method described in U.S. Pat. No. 3,188,311 affords 7-aminocephalosporanic acid (7-ACA). Acylation of 7-ACA with an appropriate acyl halide, as, for example, thiophene-2-acetyl chloride, yields the expected 7-acylamidocephalosporanic acid antibiotic. The cephalosporin antibiotics obtained from cephalosporin C according to this method are derivatives of cephalosporanic acid which possesses an acetoxymethyl group attached at the 3-position of the cephalosporin nucleus. According to the cephem nomenclature system for the cephalosporins, the cephalosporin antibiotics obtained from cephalosporin C are named 7-acylamido-3-acetoxymethyl-3-cephem-4-carboxylic acids.

The second method by which the cephalosporin antibiotics are produced involves the chemical conversion of a penicillin antibiotic. This method, described in U.S. Pat. No. 3,275,626, involves the conversion of the thiazolidine ring of a penicillin into the dihydrothiazine ring of a cephalosporin. The fused β-lactam ring of the penicillin molecule remains intact during the conversion. This chemical conversion is carried out by heating a penicillin sulfoxide in the presence of an acidic reagent, such as acetic anhydride, to obtain predominantly a 7-acylamido-3-methyl-3-cephem-4-carboxylic acid ester (a desacetoxycephalosporanic acid) and a 7-acylamido-3-methyl-3-acyloxycepham-4-carboxylic acid ester. Also produced in the chemical conversion process is a 2-acyloxymethylpenicillin, otherwise designated as a 6-acylamido-2-methyl-2-acyloxymethylpenam-3-carboxylic acid.

U.S. Pat. No. 3,275,626 additionally discusses the possibility of converting a penicillin sulfoxide by heating it in the presence of any of various acidic reagents. The ultimate antibiotic substances which form from such reactions will depend to some extent upon the particular acid which is employed, with the substituents present in the acid as well as the particular structure and relative strength of the acid having some effect upon the products formed.

In carrying out the reaction of a penicillin sulfoxide ester with thionyl chloride, it has been found that the following products can be produced:

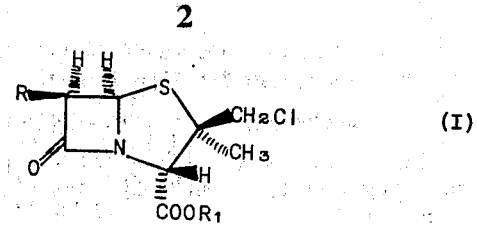

and

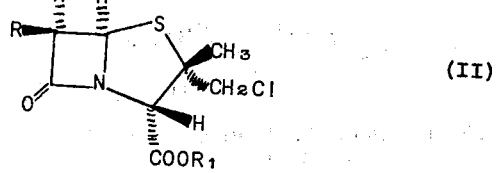

and

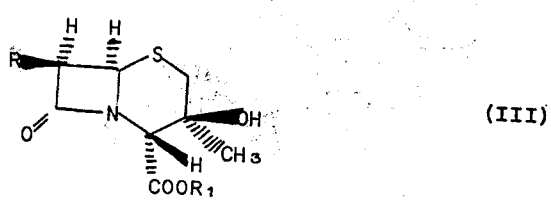

It further has been found that the 2α-methyl-2β-chloromethylpenam (I above) is unstable and gradually rearranges to the corresponding 3α-methyl-3β-chlorocepham of the formula

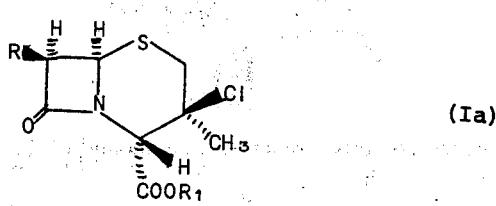

This rearrangement occurs at room temperature over a period of several days. The rearrangement can be greatly accelerated by subjecting the penam to an elevated temperature, for example, from about 50°C. to about 100°C., under which conditions the rearrangement can be accomplished in as little as one hour. Conversion to the corresponding 3α-methyl-3β-chlorocepham can also be effected by maintaining the unstable penam in a suitable inert solvent on a chromatographic column for a period of from about 24 to about 72 hours and then eluting the cepham product from the column.

In accordance with this invention, it has now been discovered that it is possible to convert a 6-imido-2α-methyl-2β-halomethylpenam-3-carboxylic acid ester having a structure such as (I) above and/or a 7-imido-3α-methyl-3β-halocepham-4-carboxylic acid ester obtainable by rearrangement from the aforementioned 2β-halomethylpenam and having a structure such as (Ia) above to an active 3-methyl-3-cephem antibiotic, a 3-methyl-3-nitrooxycepham, and a 2-methyl-2-nitrooxymethylpenam (penicillin) ring structure.

SUMMARY OF THE INVENTION

The present invention is directed to a process for preparing a mixture comprising a compound of the formula IV

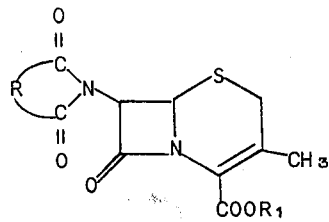

a compound of the formula V

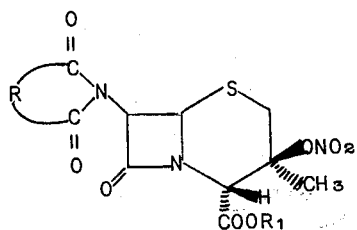

and a compound of the formula VI

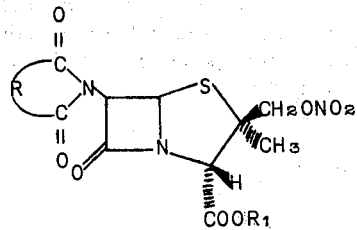

which comprises reacting a compound of the formula

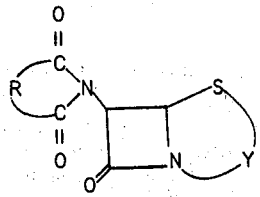

in which Y is

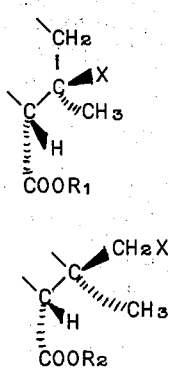

or a mixture of the two, with silver nitrate, in which, in the above formulae, R is the residue of an imide derived from a dicarboxylic acid, $R_1$ is a carboxy protecting group, and X is chlorine or bromine.

This invention is also directed to a novel nitrooxycepham compound of the formula

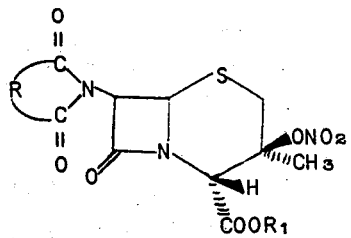

in which R and $R_1$ are as herein defined.

Another aspect of this invention involves a process for preparing a desacetoxycephalosporin of the formula

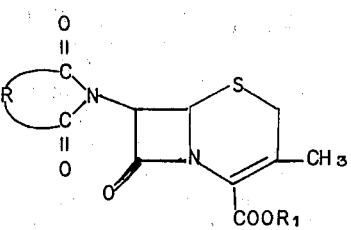

which comprises heating a nitrooxycepham compound of the formula

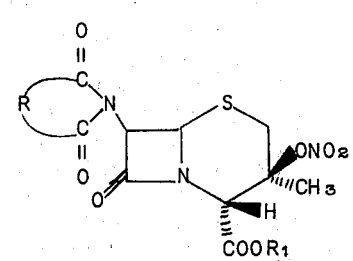

at a temperature of from about 80°C. to about 175°C. for a period sufficient to denitrate said nitrooxycepham, in which, in the above formulae, R and $R_1$ are as herein defined.

The term "nitrooxy" as used herein refers to the group $-ONO_2$. The compounds thereby defined herein can thus be considered to be nitrate esters.

DETAILED DESCRIPTION OF THE INVENTION

The process of this invention is carried out by contacting a 6-imido-2α-methyl-2β-halomethylpenam-3-carboxylic acid ester and/or a 7-imido-3α-methyl-3β-halocepham-4-carboxylic acid ester with silver nitrate. The reaction preferably is carried out at a temperature within the range of from about 0°C. to about 100°C. More preferably, the temperature of reaction is between 20°C. and 70°C. Typically, the reaction is very rapid, and the time of reaction ranges from about 5 minutes to about 1 hour, with the reaction time to some degree being dependent upon the particular reactants which are employed as well as the temperature at which the reaction is carried out. Normally, the higher the temperature of reaction the shorter the necessary reaction time. Usually, the reaction is complete after the reactants have been maintained at the selected reaction temperature for about 5–10 minutes.

The conversion of the 2-halomethylpenam and/or the 3-halocepham compound preferably is carried out in the presence of a suitable solvent, specifically one which is inert to the reactants and which will facilitate adequate mixing of the reactants. Suitable solvents are those which are capable of dissolving both the silver salt and the halomethylpenam and/or the halocepham compound and which have a boiling point at least as high as the intended temperature of reaction. Such solvents include, for example, ketones, such as acetone, and the like, and lower alkyl carboxylic acids such as acetic acid, propionic acid, butyric acid, isobutyric acid, and the like.

The conversion of the 2-halomethylpenam and/or the 3-halocepham compound is accomplished in the presence of silver nitrate. The reaction is equimolar, and therefore at least one mole of silver nitrate is required per each mole of the 2-halomethylpenam and/or 3-halocepham. Usually from about one to about two moles of silver nitrate per mole of the halo compound will be employed, and, preferably, an excess of silver nitrate will be present, such as, for example, from about 1.1 to about 1.5 moles of silver nitrate per each mole of the halo compound.

As mentioned hereinabove, the halo compounds used as starting material in the process of this invention can be prepared using techniques described in U.S. Pat. No. 3,275,626. These compounds also are available in accordance with the process described in U.S. application Ser. No. 455,444 filed of even date herewith. This process involves the reaction of a 7-imido-3α-methyl-3β-hydroxycepham-4-carboxylic acid ester with a halogen reagent in the presence of an alkaline reagent to produce the 2-halomethylpenam starting material of the process of this invention. This penam starting material will rearrange over a period of time to the corresponding 3-halocepham starting material.

The 2-halomethylpenam starting material has the formula:

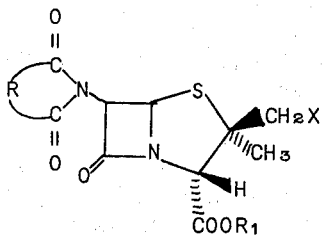

and the 3-halocepham starting material has the following formula:

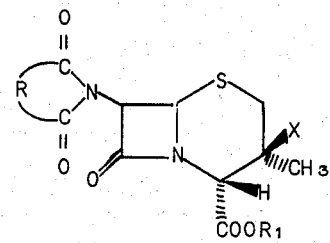

$R_1$ in the above formulae as well as in the products of the process of this invention and in the compounds of this invention denotes a carboxy protecting group. The nature of the carboxy protecting group is not important, and any of those known in the art can be used. Preferably, however, this group is the residue of an ester function which is removable by acid treatment or by hydrogenation. Preferred carboxy protecting groups include, for example, $C_1$–$C_4$ alkyl, 2,2,2-trihaloethyl, benzyl, p-nitrobenzyl, succinimidomethyl, phthalimidomethyl, p-methoxybenzyl, benzhydryl, $C_2$–$C_6$ alkanoyloxymethyl, or phenacyl, in any of the above of which halo denotes chlorine, bromine, or iodine.

Specific illustrations of the preferred ester residues of the carboxyl group of the 3-halocepham compound used in the process of this invention include, for example, methyl, ethyl, n-propyl, isopropyl, n-butyl, sec-butyl, isobutyl, t-butyl, 2,2,2-trichloroethyl, 2,2,2-tribromoethyl, benzyl, p-nitrobenzyl, succinimidomethyl, phthalimidomethyl, p-methoxybenzyl, benzhydryl, acetoxymethyl, pivaloyloxymethyl, propionoxymethyl, phenacyl, and the like.

Highly preferred ester residues are methyl, benzyl, p-nitrobenzyl, p-methoxybenzyl, benzhydryl, and 2,2,2-trichloroethyl.

In the above formulae as well as in those depicting the products of the process of this invention, the cyclic imide radical defined by R taken together with the nitrogendicarbonyl combination to which it is bonded can be obtained by reacting the precursor of the penam or cepham starting material, such as the 6-amino group of 6-aminopenicillanic acid (6-APA) or an ester of 6-APA with a dicarboxylic acid or anhydride or other reactive variant thereof, and treating the resulting derivative with a $C_1$–$C_4$ alkyl haloformate, for example, ethyl chloroformate, in the presence of an organic base.

Preferably, R is $C_2$–$C_4$ alkylene, $C_2$–$C_4$ alkenylene, —$CH_2$-Y-$CH_2$— in which Y is oxygen or sulfur, 1,2-cyclohexylene, 1,2-phenylene, 1,2-cyclohexenylene, or substituted derivatives of any of these having from 1 to 4 substituents selected from the group consisting of $C_1$–$C_3$ alkyl, $C_1$–$C_3$ alkoxy, and nitro. More preferably, R is $C_2$–$C_4$ alkylene, $C_2$–$C_4$ alkenylene, —$CH_2$-Y-$CH_2$— in which Y is oxygen or sulfur, 1,2-cyclohexylene, 1,2-phenylene, or 1,2-cyclohexenylene, each of which is unsubstituted or singly substituted with any of the aforementioned substituents. Typically, R represents the residue of a $C_4$ to $C_{10}$ dicarboxylic acid, and the cyclic imide thus represented is prepared from such dicarboxylic acid, its anhydride, or an appropriate reactive variant thereof. Cyclic imides can be prepared, for example, from acids such as succinic, maleic, glutaric, diglycolic, thiodiglycolic, phthalic, and the like, as well as from cyclohexane-1,2-dicarboxylic, 3-cyclohexene-1,2-dicarboxylic, alkyl substituted dicarboxylic acids or anhydrides such as 4,5-dimethylphthalic, tetramethylphthalic, 4-methylphthalic, nitro substituted dicarboxylic acids and anhydrides such as 3-nitrophthalic acid, alkyl substituted dicarboxylic acids and anhydrides such as methylmaleic acid, as well as related compounds and compounds of similar reactivities. Additional examples of cyclic anhydrides of the type defined are found in the prior art such as in the *Journal of Organic Chemistry*, Volume 26, pp. 3365–3367 (September, 1961). 6-Phthalimidopenicillanic acid can also be prepared from 6-APA and N-carboethoxyphthalimide according to the procedure of Y. G. Perron et al., *Journal of Medicinal Chemistry*, Volume 5, (1962), p. 1016.

The thus-produced 6imido-substituted penicillanic acid or ester can then be oxidized in accordance with known techniques to produce the penicillin sulfoxide. This sulfoxide, having an appropriate carboxy protecting group, can then be reacted in accordance with the teaching provided in U.S. Pat. No. 3,275,626 to produce the 2-halomethylpenam or 3-halocepham starting material.

The halo of the 2-halomethylpenam or the 3-halocepham starting material can be chlorine or bromine. The identity of the halogen in the starting material is determined by the particular halogen reagent which is used in the hereinbefore described processes for obtaining the 2-halomethylpenam or the 3-halocepham. Preferably, the starting material will be an ester of 6-imido-2α-methyl-2β-chloromethylpenam-3-carboxylic acid or an ester of 7-imido-3α-methyl-3β-chlorocepham-4-carboxylic acid.

The reaction of the 2-halomethylpenam and/or the 3-halocepham compound in accordance with the process of this invention accomplishes the production of a desacetoxycephalosporin (3-methyl-3-cephem). Furthermore, the reaction of the penam or cepham compound with slver nitrate produces a novel 3-nitrooxycepham compound and a 2-nitrooxymethylpenam compound.

The 2α-methyl-2β-nitrooxymethylpenam compounds produced by the process of this invention are unstable in a manner analogous to that described hereinabove with respect to the 2α-methyl-2β-chloromethylpenam compounds. The 2α-methyl-2β-nitrooxymethylpenam compounds rearrange over a period of time typically from about 24 to about 72 hours, to their corresponding 3α-methyl-3β-nitrooxycepham compounds, that is, to the same 3α-nitrooxycepham compound produced by the process of this invention.

The 3-nitrooxycepham compound itself is quite labile and is useful as an intermediate in the production of active antibiotics since, upon application of heat, it is readily converted to its corresponding desacetoxycephalosporin.

The novel 3-nitrooxycepham compounds of this invention generally are solids isolable from the reaction mixture by known techniques including, for example, chromatographic separation. The 3-nitrooxycepham is readily convertible to the corresponding 3-methyl-3-cephem compounds by application of heat. Generally, the 3-nitrooxycepham compound is dissolved in a suitable inert solvent, and the resulting solution is heated. Suitable solvents include, for example, amides, such as N,N-dimethylformamide and N,N-dimethylacetamide, hydrocarbons, such as tolune and xylene, and other approxpriate inert solvents. Typically, the nitrooxycepham is heated to a temperature of from about 100°C. to about 200°C., and preferably from about 140°C. to about 170°C. The nitrooxycepham is maintained at the elevated temperature for a time sufficient to achieve denitration and formation of the 3-methyl-3-cephem (desacetoxycephalosporin). The product is then removed from the reaction mixture by techniques well recognized in the art.

The desacetoxycephalosporins produced by this invention are convertible to active antibiotics by cleavage of the ester function in the 4-position. Deesterification can be achieved by treating the ester with an acid such as trifluoroacetic acid, hydrochloric acid, and the like, or with zinc and acid, such as formic acid, acetic acid, or hydrochloric acid. It can likewise be accomplished by hydrogenating the ester in the presence of palladium, rhodium, or a compound thereof, in suspension or on a carrier such as barium sulfate, carbon, alumina, or the like.

Furthermore, other active antibiotics can be obtained from the previously or subsequently deesterified 3-methyl-3-cephem compound either by opening the 7-imido substituent to form a 7-amido derivative or by cleaving the 7-imido substituent and acylating the resulting 7-aminodesacetoxycephalosporin (7-ADCA). Any of these conversions are accomplished using recognized techniques.

Representative of the product conversions which are available in accordance with the process of this invention are the following. It will be understood, however, that the ratio of products may vary depending upon the particular reactants which are employed, the relative quantities of reactants, and the conditions of reaction.

Methyl 6-phthalimido-2α-methyl-2β-chloromethylpenam-3-carboxylate and/or methyl 7-phthalimido-3α-methyl-3β-chlorocepham-4-carboxylate to methyl 7-phthalimido-3-methyl-3-cephem-4-carboxlate, methyl 7-phthalimido-3α-methyl-3β-nitrooxycepham-4-carboxylate, and methyl 6-phthalimido-2α-methyl-2β-nitrooxymethylpenam-3-carboxylate.

2,2,2-Trichloroethyl 6-phthalimido-2α-methyl-2β-chloromethylpenam-3-carboxylate and/or 2,2,2-trichloroethyl 7-phthalimido-3α-methyl-3β-chlorocepham-4-carboxylate to 2,2,2-trichloroethyl 7-phthalimido-3-methyl-3-cephem-4-carboxylate, 2,2,2-trichloroethyl 7-phthalimido-3α-methyl-3β-nitrooxycepham-4-carboxylate, and 2,2,2-trichloroethyl 6-phthalimido-2α-methyl-2β-nitrooxymethylpenam-3-carboxylate.

p-Nitrobenzyl 6-phthalimido-2α-methyl-2β-chloromethylpenam-3-carboxylate and/or p-nitrobenzyl 7-phthalimido-3α-methyl-3βchlorocepham-4-carboxylate to p-nitrobenzyl 7-phthalimido-3-methyl-3-cephem-4-carboxylate, p-nitrobenzyl 7-phthalimido-3α-methyl-3β-nitrooxycepham-4-carboxylate, and p-nitrobenzyl 6-phthalimido-2α-methyl-2β-nitrooxymethylpenam-3-carboxylate.

Benzyl 6-succinimido-2α-methyl-2β-chloromethylpenam-3-carboxylate and/or benzyl 7-succinimido-3α-methyl-3β-chlorocepham-4-carboxylate to benzyl 7-succinimido-3-methyl-3-cephem-4-carboxylate, benzyl 7-succinimido-3α-methyl-3β-nitrooxycepham-4-carboxylate, and benzyl 6-succinimido-2α-methyl-2β-nitrooxymethylpenam-3-carboxylate.

Benzhydryl 6-phthalimido-2α-methyl-2β-chloromethylpenam-3-carboxylate and/or benzhydryl 7-phthalimido-3α-methyl-3β-chlorocepham-4-carboxylate to benzhydryl 7-phthalimido-3-methyl-3-cephem-4-carboxylate, benzhydryl 7-phthalimido-3α-methyl-3β-nitrooxycepham-4-carboxylate, and benzhydryl 6-phthalimido-2α-methyl-2β-nitrooxymethylpenam-3-carboxylate.

t-Butyl 6-glutarimido-2α-methyl-2β-chloromethylpenam-3-carboxylate and/or t-butyl 7-glutarimido-3α-methyl-3β-chlorocepham-4-carboxylate to t-butyl 7-glutarimido-3-methyl-3-cephem-4-carboxylate, t-butyl 7-glutarimido-3α-methyl-3β-nitrooxycepham-4-carboxylate, and t-butyl 6-glutarimido-2α-methyl-2β-nitrooxymethylpenam-3-carboxylate.

p-Nitrobenzyl 6-diglycolimido-2α-methyl-2β-chloromethylpenam-3-carboxylate and/or p-nitrobenzyl 7-diglycolimido-3α-methyl-3β-chlorocepham-4-carboxylate to p-nitrobenzyl 7diglycolimido-3-methyl- 3-cephem-4-carboxylate, p-nitrobenzyl 7-diglycolimido-3α-methyl-3β-nitrooxycepham-4-carboxylate, and p-nitrobenzyl 6-diglycolimido-2α-methyl-2β-nitrooxymethylpenam-3-carboxylate.

Benzhydryl 6-(3'-isopropylphthalimido)-2α-methyl-2β-chloromethylpenam-3-carboxylate and/or benzhydryl 7-(3'-isopropylphthalimido)-3α-methyl-3β-chlorocepham-4-carboxylate to benzhydryl 7-(3'-isopropylphthalimido)-3-methyl-3-cephem-4-carboxylate, benzhydryl 7-(3'-isopropylphthalimido)-3α-methyl-3β-nitrooxycepham-4-carboxylate, and benzhydryl 6-(3'-isopropylphthalimido)-2α-methyl-2β-nitrooxmethylpenam-3-carboxylate.

p-Nitrobenzyl 6-tetramethylphthalimido-2α-methyl-2β-chloromethylpenam-3-carboxylate and/or p-nitrobenzyl 7-tetramethylphthalimido-3α-methyl-3β-chlorocepham-4-carboxylate to p-nitrobenzyl 7-tetramethylphthalimido-3-methyl-3-cephem-4-carboxylate, p-nitrobenzyl 7-tetramethylphthalimido-3α-methyl-3β-nitrooxycepham-4-carboxylate, and p-nitrobenzyl 6-tetramethylphthalimido-2α-methyl-2β-nitrooxymethylpenam-3-carboxylate.

p-Methoxybenzyl 6-(3'-nitrophthalimido)-2α-methyl-2β-chloromethylpenam-3-carboxylate and/or p-methoxybenzyl 7-(3'-nitrophthalimido)-3α-methyl-3β-chlorocepham-4-carboxylate to p-methoxybenzyl-7-(3'-nitrophthalimido)-3-methyl-3-cephem-4-carboxylate, p-methoxybenzyl 7-(3'-nitrophthalimido)-3α-methyl-3β-nitrooxycepham-4-carboxylate, and p-methoxybenzyl 6-(3'-nitrophthalimido)-2α-methyl-2β-nitrooxymethylpenam-3-carboxylate.

Phthalimidomethyl-6-(4',5'-dimethoxyphthalimido)-2α-methyl-2β-chloromethylpenam-3-carboxylate and/or phthalimidomethyl 7-(4',5'-dimethoxyphthalimido)-3α-methyl-3β-chlorocepham-4-carboxylate to phthalimidomethyl 7-(4',5'-dimethoxyphthalimido)-3-methyl-3-cephem-4-carboxylate, phthalimidomethyl 7-(4',5'-dimethoxyphthalimido)-3α-methyl-3β-nitrooxycepham-4-carboxylate, and phthalimidomethyl 6-(4',5'-dimethoxyphthalimido)-2α-methyl-2β-nitrooxymethyl-penam-3-carboxylate.

Succinimidomethyl 6-hexahydrophthalimido-2α-methyl-2β-chloromethylpenam-3-carboxylate and/or succinimidomethyl 7-hexahydrophthalimido-3α-methyl-3β-chlorocepham-4-carboxylate to succinimidomethyl 7-hexahydrophthalimido-3-methyl-3-cephem-4-carboxylate, succinimidomethyl 7-hexahydrophthalimido-3α-methyl-3β-nitrooxycepham-4-carboxylate, and succinimidomethyl 6-hexahydrophthalimido-2α-methyl-2β-nitrooxymethylpenam-3-carboxylate.

p-Nitrobenzyl 6-diglycolimido-2α-methyl-2β-chloromethylpenam-3-carboxylate and/or p-nitrobenzyl 7-diglycolimido-3α-methyl-3β-chlorocepham-4-carboxylate to p-nitrobenzyl 7-diglycolimido-3-methyl-3-cephem-4-carboxylate, p-nitrobenzyl 7-diglycolimido-3α-methyl-3β-nitrooxycepham-4-carboxylate, and p-nitrobenzyl 6-diglycolimido-2α-methyl-2β-nitrooxymethylpenam-3-carboxylate.

Pivaloyloxymethyl 6-(1',2',3',6'-tetrahydrophthalimido)-2α-methyl-2β-chloromethylpenam-3-carboxylate and/or pivaloyloxymethyl 7-(1',2',3',6'-tetrahydrophthalimido)-3α-methyl-3β-chlorocepham-4-carboxylate to pivaloyloxymethyl 7-(1',2',3',6'-tetrahydrophthalimido)-3-methyl-3-cephem-4-carboxylate, pivaloyloxymethyl 7-(1',2',3',6'-tetrahydrophthalimido)-3α-methyl-3β-nitrooxycepham-4-carboxylate, and pivaloyloxymethyl 6-(1',2',3',6'-tetrahydrophthalimido)-2α-methyl-2β-nitrooxymethylpenam-3-carboxylate.

Acetoxymethyl 6-(3'-methylphthalimido)-2α-methyl-2β-chloromethylpenam-3-carboxylate and/or acetoxymethyl 7-(3'-methylphthalimido)-3α-methyl-3β-chlorocepham-4-carboxylate to acetoxymethyl 73'-methylphthalimido)-3-cephem-4-carboxylate, acetoxymethyl 7-(3'-methylphthalimido)-3α-methyl-3β-nitrooxycepham-4-carboxylate, and acetoxymethyl 6-(3'-methylphthalimido)-2α-methyl-2β-nitrooxymethylpenam-3-carboxylate.

Phenacyl 6-(4'-methoxyphthalimido)-2α-methyl-2β-chloromethyl-penam-3-carboxylate and/or phenacyl 7-(4'-methoxyphthalimido)-3αmethyl-3β-chlorocepham-4-carboxylate to phenacyl 7-(4'-methoxyphthalimido)-3-methyl-3-cephem-4-carboxylate, phenacyl 7-(4'-methoxyphthalimido)-3α-methyl-3βnitrooxycepham-4-carboxylate, and phenacyl 6-(4'-methoxyphthalimido)-2α-methyl-2β-nitrooxymethylpenam-3-carboxylate.

p-Nitrobenzyl 6-thioglycolimido-2α-methyl-2β-chloromethyl-penam-3-carboxylate and/or p-nitrobenzyl 7-thioglycolimido-3α-methyl-3β-chlorocepham-4-carboxylate to p-nitrobenzyl 7-thioglycolimido-3-methyl3α-cephem-4-carboxylate, p-nitrobenzyl 7-thioglycolimido-3α-methyl-3β-nitrooxycepham-4-carboxylate, and p-nitrobenzyl 6-thioglycolimido-2α-methyl-2β-nitrooxymethylpenam-3-carboxylate.

Phenacyl 6-glutarimido-2α-methyl-2β-chloromethylphenam-3-carboxylate and/or phenacyl 7-glutarimido-3α-methyl-3β-chlorocepham-4-carboxylate to phenacyl 7-glutarimido-3-methyl-3-cephem-4-carboxylate, phenacyl 7-glutarimido-3α-methyl-3β-nitrooxycepham-4-carboxylate, and phenacyl 6-glutarimido-2α-methyl-2β-nitrooxymethylpenam-3-carboxylate.

2,2,2-Trichloroethyl 6-(3'-isopropylphthalimido)-2α-methyl-2β-chloromethylpenam-3-carboxylate and/or 2,2,2-trichloroethyl 7-(3'-isopropylphthalimido)-3α-methyl-3β-chlorocepham-4-carboxylate to 2,2,2-trichloroethyl 7-(3'-isopropylphthalimido)-3-methyl-3-cephem-4-carboxylate, 2,2,2-trichloroethyl 7-(3'-isopropylphthalimido)-3α-methyl-3β-nitrooxycepham-4-carboxylate, and 2,2,2-trichloroethyl 6-(3'-isopropylphthalimido)-2α-methyl-2β-nitrooxymethylpenam-3-carboxylate.

p-Methoxybenzyl 6-(3'-methoxyphthalimido)-2α-methyl-2β-chloromethylpenam-3-carboxylate and/or p-methoxybenzyl 7-(3'-methoxyphthalimido)-3α-methyl-3β-chlorocepham-4-carboxylate to p-methoxybenzyl 7-(3'-methoxyphthalimido)-3-methyl-3-cephem-4-carboxylate, p-methoxybenzyl 7-(3'-methoxyphthalimido)-3α-methyl-3β-nitrooxycepham-4-carboxylate, and p-methoxybenzyl 6-(3'-methoxyphthalimido)-2α-methyl-2β-nitrooxymethylpenam-3-carboxylate.

p-Nitrobenzyl 6-(1',4',5',6'-tetrahydrophthalimido)-2α-methyl-2β-chloromethylpenam-3-carboxylate and/or p-nitrobenzyl 7-(1',4',5',6'-tetrahydrophthalimido)-3α-methyl-3β-chlorocepham-4-carboxylate to p-nitrobenzyl 7-(1',4',5',6'-tetrahydrophthalimido)-3-methyl-3-cephem-4-carboxylate, p-nitrobenzyl 7-(1',4',5',6'-tetrahydrophthalimido)-3α-methyl-3β-nitrooxycepham-4-carboxylate, and p-nitrobenzyl 6-(1',4',5',6'-tetrahydrophthalimido)-2α-methyl-2β-nitrooxymethylpenam-3-carboxylate.

It will be understood that, in the above representative conversions, a corresponding 2α-bromomethylpenam and/or 3 -bromocepham reactant can be substituted for any of the mentioned 2β-chloromethylpenam and/or 3-chlorocepham reactants.

The products produced in accordance with the process of this invention can be isolated by conventional methods. These can include, for example, chromatographic separation, filtration, recrystallization, and the like.

This invention is further illustrated by references to the examples which follow. It is not intended that this invention be limited in scope by reason of any of the examples provided herein.

Preparation of Methyl 6-Phthalimido-2α-methyl-2β-chloromethylphenam-3-carboxylate A solution of 2.25 g. (6 mmol) of methyl 6-phthalimido-2,2-dimethylphenam-3-carboxylate-1-oxide, 0.47 ml. (6.5 mmol) thionyl chloride, and 0.84 ml. (6 mmol) of triethylamine in 90 ml. of dry carbon tetrachloride was refluxed for 1 hr. The reaction mixture was then cooled and evaporated in vacuo to give a light yellow foam. Chromatography on 70 g. of acid washed silica gel yielded three fractions, the first of which contained 780 mg. (33%) of methyl 6-phthalimido-2α-methyl-2β-chloromethylphenam-3-carboxylate. Recrystallization from diethyl ether gave colorless needles: mp 107°–112°; $[\alpha]^{27}$ D 225.4° ($CH_3CH$); ir ($CHCl_3$) 1802 (β-lactam C=O), 1732 and 1785 (phthalimido C=O) and 1748 $cm^{-1}$ (ester C=O); nmr ($CDCl_3$) 95 (s, 3, 3-$CH_3$), 230 (s, Me ester), 246 (ABq, 2, J=24 Hz and J=12 Hz), 307 (s, 1, H-4), 344 (s, 2, β-lactam H's) and 472 Hz (m, 4, ArH).

Anal. Calcd for $C_{17}H_{15}ClN_2O_5S$: C, 51.71; H, 3.83; N, 7.10; O, 20.26; S, 8.12; Cl, 8.98. Found: C, 52.00; H, 4.01; N, 7.24; O, 20.25; S, 7.76; Cl, 9.04.

The second fraction (210 mg.) contained a 3:1 mixture (by nmr) of the 2β-chloromethylpenam methyl ester and the isomeric methyl 6-phthalimido-2α-chloromethylpenam-2β-methyl-3-carboxylate. The latter was obtained from a third fraction as a white foam (250 mg., 11%) which was recrystallized from $Et_2O$ to give colorless needles: mp 166°–167°; $[\alpha]^{27}$ D 221.0° ($CH_3CN$); ir ($CHCl_3$) 1803 (β-lactam C=O), 1745 and 1786 (phthalimido C=O), and 1737 $cm^{-1}$ (ester C=O); nmr ($CDCl_3$) 116 (s, 3, β-methyl), 229 (s, 3, methyl ester), 231 (ABq, 2, J=15 and J=11.5 Hz, $CH_2Cl$), 286 (s, 1, H–3), 340 (q, 2, J=4 Hz, β-lactam H's) and 470 Hz (m, 4, ArH).

Anal. Calcd for $C_{17}H_{15}ClN_2O_5S$: C, 51.71; H, 3.83; N, 7.10. Found C, 51.91; H, 3.72; N, 7.18.

Preparation of p-Nitrobenzyl 6-Phthalimido-2α-methyl-2β-chloromethylpenam-3-carboxylate A solution of 497 mg. (1 mmol) of p-nitrobenzyl 6-phthalimido-2,2-dimethylpenam-3-carboxylate-1-oxide, 0.105 ml. of thionyl chloride, and 0.14 ml. (1 mmol) of triethylamine in 25 ml. of dry 1,2-dichloroethane was refluxed for 45 min. The mixture was cooled and the solvent evaporated. The residue was taken up in 25 ml. of ethyl acetate and the insoluble salt filtered, the filtrate washed with water and brine, and the organic extract dried and evaporated. The mixture was chromatographed over a silicia gel column to obtain p-nitrobenzyl 6-phthalimido-2α-methyl-2β-chloromethylpenam-3-carboxylate and and p-nitrobenzyl 6-phthalimido-2α-chlorometylypenam-2β-methyl-3-carboxylate identified by nmr spectra.

Preparation of p-Nitrobenzyl 6-Phthalimido-2α-methyl-2β-chloromethylpenam-3-carboxylate Triethylamine (1.2 ml., 8.8 mmol) in 20 ml. of 1,2-dichloroethane was added dropwise to a refluxing solution of p-nitrobenzyl 7-pthalimido-3α-methyl-3β-hydroxycepham-4-carboxylate (3.98 g., 8 mmol) and thionyl chloride (0.7 ml., 9 mmol) in 250 ml. of 1,2-dichloroethane. After 1 hour at reflux, another 0.5 thionyl chloride and 0.5 ml. triethylamine were added to the reaction mixture. After 2 more hours at reflux the dark brown mixture was cooled. Analysis of the dark brown mixture by nmr showed it to contain p-nitrobenzyl 6-phthalimido-2α-methyl-2β-chloromethylpenam-3-carboxylate and as minor products, p-nitrobenzyl 6-phthalimido-2α-chloromethylpenam-2β-methyl-3-carboxylate and p-nitrobenzyl 7-phthalimido-3-methyl-3-cephem-4-carboxylate. The mixture was evaporated in vacuo to dryness. The crude product was then taken up in 80 ml. chloroform, refluxed with 7 g. of decolorizing carbon and filtered. The filtrate was washed with water (2 × 50 ml.) and brine (50 ml.), dried and evaporated in vacuo to dryness. Recrystallization from ethyl acetate/diethyl ether/pet. ether gave 2.3 g. (56%) of p-nitrobenzyl 6-phthalimido-2α-methyl-2β-chloromethylpenam-3-carboxylate as tan needles (mp 161°–163°): nmr ($CDCl_3$) 93 (3, s, 3-$CH_3$), 220 and 270 (2, ABq, J=12 Hz), 311 (1, s, 4-H), 319 (2, s, ester $CH_2$), 343 (2, s, β-lactam protons), and 478 Hz (8, m, ArH); ir ($CHCl_3$) 1809 (β-lactam C=O), 1735 (ester C=O), 1743 (s) and 1787 $cm^{-1}$ (phthalimido C=O).

Anal. Calcd for $C_{23}h_{18}N_3ClO_7S$: C, 53.53; H, 3.52; N, 8.14; Cl, 6.87. Found: C, 53.70; H, 3.65; N, 8.33; Cl, 6.90.

Preparation of p-Methoxybenzyl 6-Phthalimido-2α-methyl-2β-chloromethylpenam-3-carboxylate A solution of p-methoxybenzyl 6-phthalimido-2,2-dimethylpenam-3-carboxylate-1-oxide (964 mg., 2 mmol), thionyl chloride (0.17 ml., 2.2 mmol) and triethylamine (0.28 ml., 2 mmol) in 40 ml. of dry 1,2-dichloroethane was refluxed for 50 minutes, cooled and evaporated in vacuo to dryness. The product residue was taken up in 50 ml. ethyl acetate, washed with water (50 ml.) and brine (50 ml.), dried ($MgSO_4$) and evaporated in vacuo to dryness. Both p-methoxybenzyl 6-phthalimido-2α-methyl-2β-chloromethylpenam-3-carboxylate and p-methyloxybenzy 6-phthalimido-2α-chloromethylpenam-2β-methyl-3-carboxylate were identified by nmr spectroscopy.

Preparation of p-Methoxybenzyl 6-Phthalimido-2α-methyl-2β-chloromethylpenam-3-carboxylate Triethylamine (2.10 ml., 15 mmol), in 50 ml. 1,2-dichloroethane was added dropwise to a refluxing solution of p-methoxybenzyl 7-phthalimido-3α-methyl-3β-hydroxycepham-4-carboxylate (7.23 g., 15 mmol) and thionyl chloride (1.30 ml., 16 mmol) in 400 ml. of 1,2-dichloroethane. After 90 minutes at reflux another 0.3 ml. of thionyl chloride and 0.2 ml. of triethylamine were added to the reaction mixture. The mixture was then refluxed for an additional 30 minutes and cooled. The crude reaction mixture contains p-methoxybenzyl 6-phthalimido-3α-chloromethylpenam-2β-methyl-3-carboxylate and p-methoxybenzyl 7-phthalimido-3-methyl-3-cephem-4-carboxylate as minor products and p-methyloxybenzyl 6-phthalimido-2α-methyl-2β-chloromethylpenam-3-carboxylate as the major product. The mixture was evaporated to dryness. The crude product was chromatographed on a silica gel column (250 g., 4 × 35 cm.) which was developed with 6% benzene in ethyl acetate taking 22 ml. fractions every 15 minutes. A total of 4.5 grams (60%) of p-methoxybenzyl 6-phthalimido-2α-methyl-2β-chloromethylpenam-3-carboxylate was obtained: nmr (CDCl$_3$) 90 (3, s, 3-CH$_3$), 229 (3, s, OCH$_3$), 219 and 267 (s, ABq, J= 12 Hz, 2C-CH$_2$), 306 (1, s, 4-H), 310 (2, s, ester CH$_2$) 343 (2, s, azetidinone protons), 426 (4, q, benzyl ArH), and 469 Hz (4, m, phthalimido H); ir (CHCl$_3$) 1806 (azetidinone C=O), 1736 (ester C=O), and 1745, 1788 cm$^{-1}$ (phthalimido C=O).

Anal. Calcd for C$_{24}$H$_{21}$N$_2$ClO$_6$S: C, 57.54; H, 4.23; N, 5.59; S, 6.40; Cl, 7.08. Found: C, 57.35; H, 4.42; N, 5.42; S, 6.19; Cl, 7.79.

EXAMPLE I

A solution of p-nitrobenzyl 6-phthalimido-2α-methyl-2β-chloromethylpenam-3-carboxylate (2.06 g., 4 mmol) and silver nitrate (1.0 g., ~6 mmol) in 150 ml. of acetone was refluxed for one-half hour, cooled and evaporated in vacuo to dryness. The product was taken up in 250 ml. of chloroform, heated to reflux, and filtered. The filtrate was evaporated in vacuo to dryness. An nmr spectrum of the crude mixture showed three products: p-nitrobenzyl 7-phthalimido-3α-methyl-3β-nitrooxycepham-4-carboxylate, p-nitrobenzyl 6-phthalimido-2α-methyl-2β-nitrooxymethylpenam-3-carboxylate, and p-nitrobenzyl 7-phthalimido-3-methyl-3-cephem-4-carboxylate in a ratio of ca. 13:3:1, respectively.

EXAMPLE II

A solution of p-methoxybenzyl 6-phthalimido-2α-methyl-2β-chloromethylpenam-3-carboxylate (2.50 g., 5 mmol) and siliver nitrate (1.2 g., 7 mmol, powdered) in 130 ml. of acetone was refluxed on a steam bath for 30 minutes, cooled, and evaporated to dryness. Chloroform (100 ml.) was added, and the mixture was heated to near reflux. Silver chloride which formed was filtered, and the filtrate was evaporated in vacuo to dryness. An nmr of the resulting colorless foam indicated a 20:6:2:1 ratio of p-methoxybenzyl 7-phthalimido-3α-methyl-3β-nitrooxycepham-4-carboxylate: p-methoxybenzyl 6-phthalimido-2α-methyl-2β-nitrooxymethylpenam-3-carboxylate: p-methoxybenzyl 6-phthalimido-2α-nitrooxymethylpenam-2β-methyl-3-carboxylate: p-methoxybenzy 7-phthalimido-3-methyl-3-cepham-4-carboxylate, repectively. Chromatography on a 2½X 44 cm. silica gel (80 g.) column developed with 5% benzene/ethyl acetate gave 420 mg. (16%) of p-methoxybenzyl 6-phthalimido-2α-methyl-2β-nitrooxymethylpenam-3-carboxylate as a white foam:nmr (CDCl$_3$) 85 (3, s, 2α-CH$_3$) 229 (3, s, OCH$_3$), 278 and 306 (2, ABq, J=11 Hz, 2β-CH$_2$ONO$_2$), 295 (1, s, 3-H), 311 (2, s, ester CH$_2$), 343 (2, s, azetidinone protons), 426 (4, q, ester ArH) and 469 Hz (4, m, phthalimido H): ir (CHCl$_3$) 1651 (nitrate), 1736 (ester C=O), 1745 and 1788 (phthalimido C=O) and 1810 cm$^{-1}$ (azetidinone C=O).

Anal. Calcd for C$_{24}$H$_{21}$N$_3$O$_9$S: C, 54.65; H, 4.01; N, 7,97; O, 27.30; S, 6.08. Found: C, 54.38; H, 4.10; N, 7.98; O, 27.16; S, 5.86.

The next fractions contained 120 mg. of a 3:2 mixture of the 2α-nitrooxymethylpenam and the corresponding 2β-nitrooxymethylpenam, respectively.

The last fractions contained 1.54 g. of a 3:1 mixture of p-methoxybenzyl 7-phthalimido-3α-methyl-3β-nitrooxycepham-4-carboxylate and p-methoxybenzyl 7-phthalimido-3-methyl-3-cephem-4-carboxylate, respectively. The compounds were identified by nmr spectroscopy and are separable by chromatography.

EXAMPLE III p-Methoxybenzyl 7-phthalimido-3α-methyl-3β-nitrooxycepham-4-carboxylate (250 mg.) from Example II in 4 ml. of N,N-dimethylformamide was heated to reflux for 20 minutes. After cooling, water (40 ml.) and ethyl acetate (40 ml.) were added to the reaction mixture. The organic layer was separated a washed with water (2 × 60 ml.) and brine (50 ml.) and then dried over MgSO$_4$. Evaporation in vacuo produced a light yellow foam (212 mg.) containing no starting material and identified as p-methoxybenzyl 7-phthalimido-3-methyl-3-cephem-4-carboxylate: nmr (CDCl$_3$) 139 (3, s, 3-CH$_3$), 179 and 223 (2, ABq, J=16 Hz, 2-CH$_2$), 229 (3, s, OCH$_3$), 307 (1, d, J=4 Hz, acetidinone H), 343 (1, d, J=4 Hz, azetidinone H), 430 (4, q, ester ArH), and 471 Hz (4, m, phthalolyl H).

Example IV

A solution of silver nitrate (0.85 g., 5 mmol) and methyl 6-phthalimido-2α-methyl-2β-chloromethylpenam-3-carboxylate (1.17 g., 3 mmol) in 80 ml. of acetone was refluxed for 20 minutes, cooled, and filtered. The filtrate was evaporated in vacuo to dryness. An nmr spectrum of the crude product showed approximately a 15:5:1 mixture of methyl 7-phthalimido-3α-methyl-3β-nitrooxycepham-4-carboxylate, methyl 6-phthalimido-2α-methyl-2β-nitrooxymethylpenam-3-carboxylate and methyl 7-phthalimido-3-methyl-3-cephem-4-carboxylate, respectively. Chromatography of the product mixture on silica gel gave methyl 6-phthalimido-2α-methyl-2β-nitrooxymethylpenam-3-carboxylate (260 mg., 20% yield) which crystallized from chloroform to give colorless prisms (mp 115.5°–117.5°C.): nmr (CDCl$_3$) 92 (s, 3, 2α-CH$_3$), 231 (s, 3, ester CH$_3$), 280 and 310 (ABq, 2, J=11 Hz, 2β -CH$_2$), 297 (s, 1, 3-H), 346 (s, 2, azetidinone H's, and 470 Hz (m, 4, ArH); ir (CHCl$_3$) 1803 (azetidinone C=O), 1728 (ester C=O), 1743 and 1782 (phthalimido C=O) and 1648 cm$^{-1}$ (ONO$_2$); mass spectrum (M$_-$, 421).

Anal. Calcd for C$_{17}$H$_{15}$N$_3$O$_8$S: C, 48.46; H, 3.57; N, 9.97; O, 30.37; S, 7.61. Found: C, 48.27; H, 3.62; N, 10.15; O, 30.14; S, 7.88.

A second fraction (680 mg.) was shown by nmr to be a ca. 8:1 mixture of methyl 7-phthalimido 3α-methyl-3β-nitrooxycepham-4-carboxylate and methyl 7-phthalimido-3-methyl-3-cephem-4-carboxylate, respectively. The nmr peaks assigned to methyl 7-phthalimido-3α-methyl-3β-nitrooxycepham-4-carboxylate are as follows: 106 (s, 3, 3-CH$_3$), 206 (s, 2, 2-CH$_2$), 232 (s, 3, ester CH$_3$), 306 (s, 1, 4-H), 325 and 335 (q, 2, J=4 Hz, azetidinone H's), and 470 Hz (m, 4, ArH). The ir spectrum (CHCl$_3$) exhibits a strong absorbtion at 1645 cm$^{-1}$ characteristic for the —ONO$_2$ group.

Example V

Methyl 7-phthalimido-3α-methyl-3β-nitrooxycepham-4-carboxylate (200 mg.) in 3 ml. of N,N-dimethylformamide was heated to reflux for 20 minutes. After cooling, water (30 ml.) and ethyl acetate (30 ml.) were added to the reaction mixture. The organic layer was separated and washed with water (2 × 50 ml.) and brine (50 ml.) and then dried over MgSO$_4$. Evaporation in vacuo produced a light colored foam. An nmr spectrum of this product showed complete conversion to methyl 7-phthalimido-3-methyl-3-cephem-4-carboxylate.

Example VI

Methyl 6-phthalimido-2α-methyl-2β-chloromethylpenam-3-carboxylate (1.44 g.; 3.65 mmole) was chromatographed on a 4 × 70 cm. column packed with 80 g. (15 cm.) of acid washed silica gel. The 2β-chloromethylpenam compound was washed onto the column with 100 ml. (out of a total of 200 ml) of toluene at an initial rate of 1.8 ml. per minute. The flow rate was then shut off, and the column was allowed to stand for 2.5 days. The column was then developed at 1.0 ml. per minute using a mixture containing 10 percent ethyl acetate in toluene. Fractions of 20 ml. each were collected. Fractions 41–80 gave 0.57 g. of methyl 7-phthalimido-3α-methyl-3β-chlorocepham-4-carboxylate: nmr ($CDCl_3$) 105 (s, 3, $C_3$—$\alpha CH_3$); 184, 206 (ABq, 2, $C_2$-H); 297 (s, 1, $C_4$-H); 324 (d, 1, $C_6$-H); and 337 Hz (d, 1, $C_7$-H).

Example VII

To 100 mg. (0.25 mmole) of methyl 7-phthalimido-3α-methyl-3β-chlorocepham-4-carboxylate dissolved in 25 ml. of acetone were added 100 mg. (0.59 mmole) of silver nitrate. The resulting mixture was stirred and heated to reflux for 32 hours. The reaction mixture was then evaporated in vacuo to dryness. The residue was slurried with 10 ml. of chloroform and filtered. The reacton flask and precipitate were washed with 10 ml. of chloroform, and the chloroform was added to the filtrate. The filtrate was evaporated in vacuo to dryness to yield a yellow foam. An nmr spectra was prepared, and the product distribution was obtained by integration of the methyl peaks: nmr ($CDCl_3$) 140 (s, 3, 3-$CH_3$ for $\Delta^3$ cephem); 104 (s, 3, 3α-$CH_3$ for 3β-$NO_3$ cepham); 92 Hz (s, 3, 2α-$CH_3$ for 2β-$CH_2NO_3$ penam). Product distribution was thus determined to be: methyl 7-phthalimido-3α-methyl-3β-nitrooxycepham-4-carboxylate (73 percent): methyl 7-phthalimido-3-methyl-3-cepham-4-carboxylate (17 percent); and methyl 6-phthalimido-2α-methyl-2β-nitrooxymethylpenam-3-carboxylate (10 percent).

We claim:

1. A process for preparing a mixture of a compound of the formula IV

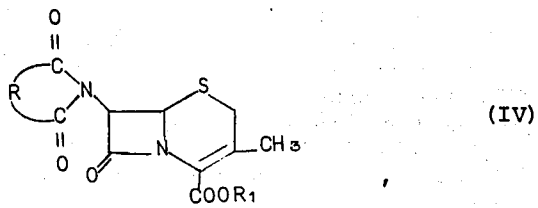
(IV)

a compound of the formula V

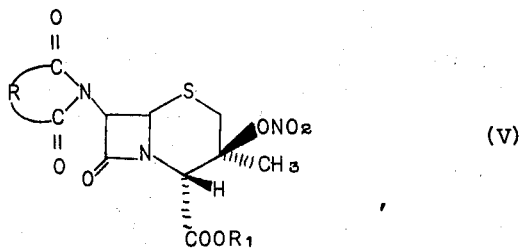
(V)

and a compound of the formula VI

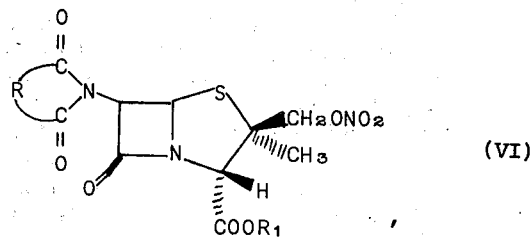
(VI)

which comprises the step of reacting a compound of the formula

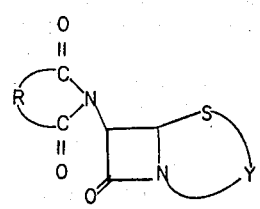

in which Y is

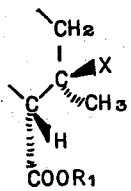

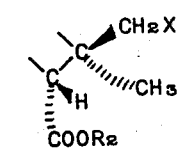

or a mixture of the two, with silver nitrate, in which, in the above formulae, R is the residue of an imide derived from a dicarboxylic acid, $R_1$ is a carboxy protecting group, and X is chlorine or bromine.

2. Process of claim 1, in which R is $C_2$–$C_4$ alkylene, $C_2$–$C_4$ alkenylene, —$CH_2$—Y—$CH_2$— in which Y is oxygen or sulfur, 1,2-cyclohexylene, 1,2-phenylene, 1,2-cyclohexenylene, or a substituted derivative of any of the above having from 1 to 4 substituents selected from the group consisting of $C_1$–$C_3$ alkyl, $C_1$–$C_3$ alkoxy, and nitro.

3. Process of claim 2, in which R is $C_2$–$C_4$ alkylene, $C_2$–$C_4$ alkenylene, —$CH_2$—Y—$CH_2$— in which Y is oxygen or sulfur, 1,2-cyclohexylene, 1,2-phenylene, or 1,2-cyclohexenylene.

4. Process of claim 3, in which $R_1$ is the residue of an ester group which is removable by hydrogenation or acid treatment.

5. Process of claim 4, in which $R_1$ is $C_1$–$C_4$ alkyl, 2,2,2-trihaloethyl, 2-iodoethyl, benzyl, p-nitrobenzyl, succinimidomethyl, phthalimidomethyl, p-methoxybenzyl, benzhydryl, $C_2$–$C_6$-alkanoyloxymethyl, or phenacyl.

6. Process of claim 5, in which Y is

7. Process of claim 5, in which Y is

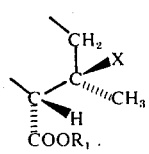

8. Process of claim 5, in which the starting material comprises a mixture in which Y is

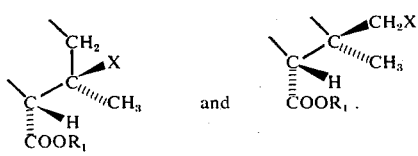

9. Process of claim 5, in which X is chloro.
10. Process of claim 9, in which R is 1,2-phenylene.
11. Process of claim 9, in which $R_1$ is methyl, benzyl, p-nitrobenzyl, p-methoxybenzyl, benzhydryl, or 2,2,2-trichloroethyl.
12. Process of claim 11, in which $R_1$ is p-nitrobenzyl.
13. Process of claim 11, in which $R_1$ is p-methoxybenzyl.
14. A compound of the formula

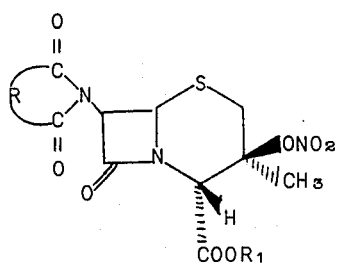

in which r is the residue of an imide derived from a dicarboxylic acid and $R_1$ is a carboxy protecting group.

15. Compound of claim 14, in which R is $C_2$–$C_4$ alkylene, 1,2-cyclohexylene, 1,2-phenylene, 1,2-cyclohexenylene, or a substituted derivative of any of the above having from 1 to 4 substituents selected from the group consisting of $C_1$–$C_3$ alkyl, $C_1$–$C_3$ alkoxy, and nitro.

16. Compound of claim 15, in which R is $C_2$–$C_4$ alkylene, $C_2$–$C_4$ alkenylene, —$CH_2$—Y—$CH_2$— in which Y is oxygen or sulfur, 1,2-cyclohexylene, 1,2-phenylene, or 1,2-cyclohexenylene.

17. Compound of claim 16, in which $R_1$ is the residue of an ester group which is removalbe by hydrogenation or acid treatment.

18. Compound of claim 17, in which $R_1$ is $C_1$–$C_4$ alkyl, 2,2,2-trihaloethyl, 2-iodoethyl, benzyl, p-nitrobenzyl, succinimidomethyl, phthalimidomethyl, p-methoxybenzyl, benzhydryl, $C_2$–$C_6$-alkanoyloxymethyl, or phenacyl.

19. Compound of claim 18, in which $R_1$ is methyl, benzyl, p-nitrobenzyl, p-methoxybenzyl, benzhydryl, or 2,2,2-trichloroethyl.
20. Compound of claim 19, in which $R_1$ is p-nitrobenzyl.
21. Compound of claim 19, in which $R_1$ is p-methoxybenzyl.
22. Compound of claim 19, in which R is 1,2-phenylene.
23. Process for preparing a desacetoxycephalosporin of the formula

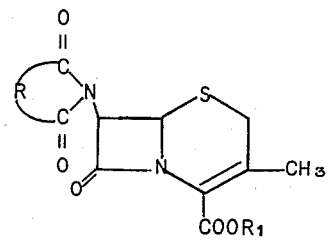

which comprises the step of heating a nitrooxycepham compound of the formula

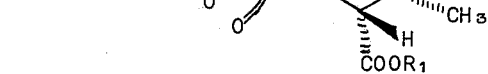

at a temperature of from about 80°C. to about 175°C. for a period sufficient to denitrate said nitrooxycepham, in which, in the above formulae, R is the residue of an imide derived from a dicarboxylic acid and $R_1$ is a carboxy protecting group.

24. Process of claim 23, in which R is $C_2$–$C_4$ alkylene, 1,2-cyclohexylene, 1,2-phenylene, 1,2-cyclohexenylene, or a substituted derivative of any of the above having from 1 to 4 substituents selected from the group consisting of $C_1$–$C_3$ alkyl, $C_1$–$C_3$ alkoxy, and nitro.

25. Process of claim 24, in which R is $C_2$–$C_4$ alkylene, $C_2$–$C_4$ alkenylene, —$CH_2$—Y—$CH_2$— in which Y is oxygen or sulfur, 1,2-cyclohexylene, 1,2-phenylene, or 1,2-cyclohexenylene.

26. Process of claim 25, in which $R_1$ is the residue of an ester group which is removable by hydrogenation or acid treatment.

27. Process of claim 26, in which $R_1$ is $C_1$–$C_4$ alkyl, 2,2,2-trihaloethyl, 2-iodoethyl, benzyl, p-nitrobenzyl, succinimidomethyl, phthalimidomethyl, p-methoxybenzyl, benzhydryl, $C_2$–$C_6$ alkanoyloxymethyl, or phenacyl.

28. Process of claim 27, in which R is 1,2-phenylene.
29. Process of claim 27, in which $R_1$ is methyl, benzyl, p-nitrobenzyl, p-methoxybenzyl, benzhydryl, or 2,2,2-trichloroethyl.
30. Process of claim 29, in which $R_1$ is p-nitrobenzyl.
31. Process of claim 29, in which $R_1$ is p-methoxybenzyl.

* * * * *